United States Patent [19]

Carpenter et al.

[11] Patent Number: 5,410,919
[45] Date of Patent: May 2, 1995

[54] REMOTELY CONTROLLED SAMPLING DEVICE HAVING A VENT PASSAGE CONNECTING AN INTERNAL CHAMBER TO THE ENVIRONMENT THROUGH AN UPPER OUTLET

[75] Inventors: Robert E. Carpenter, Nutley; Scott Santora, Hammonton; Stephen A. Borgianini, Mount Holly, all of N.J.

[73] Assignee: Norton Company, Worcester, Mass.

[21] Appl. No.: 940,414

[22] Filed: Sep. 3, 1992

[51] Int. Cl.⁶ .................................................. G01N 1/12
[52] U.S. Cl. ............................. 73/864.63; 73/864.66
[58] Field of Search .......... 73/863.01, 863.73, 864.62, 73/864.63, 864.64, 864.67, 864.66, 170.32, 170.34

[56] References Cited

U.S. PATENT DOCUMENTS

| | | | |
|---|---|---|---|
| 3,625,066 | 12/1971 | Greene | 73/425.4 |
| 3,986,553 | 10/1976 | Klyen | 73/864.66 |
| 4,037,477 | 7/1977 | Niskin | 73/864.67 |
| 4,050,315 | 9/1977 | Markfelt | 73/864.66 |
| 4,346,519 | 8/1982 | Milo | 73/864.63 |
| 4,347,751 | 9/1982 | Niskin et al. | 73/864.33 |
| 4,531,895 | 7/1985 | Zeck | 73/864.62 |
| 4,884,439 | 12/1989 | Baird | 73/864.63 |
| 4,940,088 | 7/1990 | Goldschild | 73/864.62 |
| 4,949,582 | 8/1990 | Vollweiler | 73/864.63 |

*Primary Examiner*—Richard E. Chilcot, Jr.
*Assistant Examiner*—William L. Oen
*Attorney, Agent, or Firm*—Arthur A. Loiselle; Brian M. Kolkowski; Stephen L. Borst

[57] ABSTRACT

A remotely controlled fluid sampling device adapted to take and retrieve samples from any depth or level within a body of fluid comprises an elongated tubular container, the upper outlet end of which is sealingly attached to an end cap. The end cap has a vent passage, a drain passage, a manually operated stop cock for opening and closing off the drain passage, and an eye or hook portion for attaching a support means thereto. A sealed housing is sealingly attached to the opposite inlet end portion of the tubular container and encloses an upper valve chamber with a fluid passage in its outer wall and a lower power chamber separated by an upper end wall in which a valve bore is sealingly engaged by an axially moveable valve stem. The valve stem is connected to the drive shaft of reversible power means sealed within the power chamber and which selectively moves the valve stem into and out of engagement with a valve seat and thereby opens and closes a valve passage therein connected to the internal chamber of the tubular container.

9 Claims, 1 Drawing Sheet

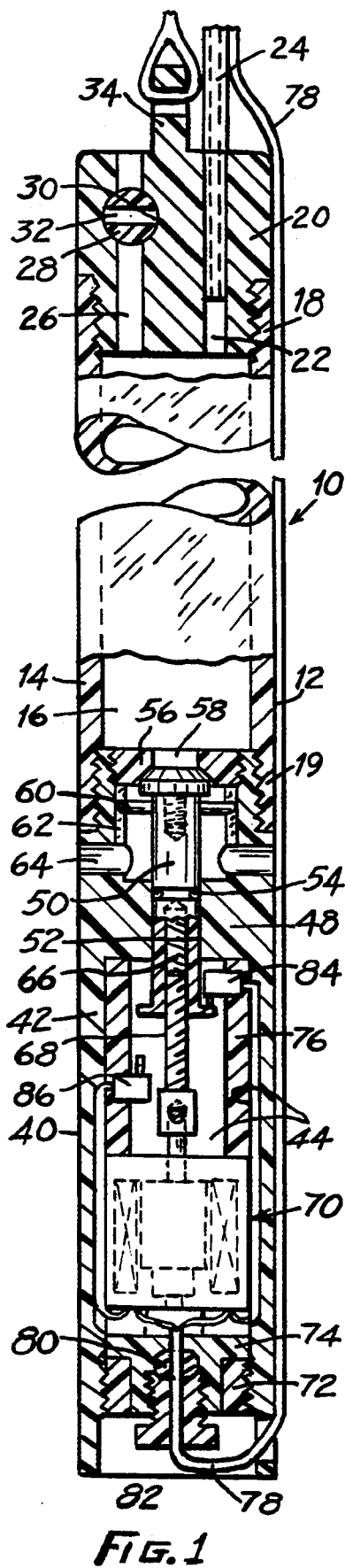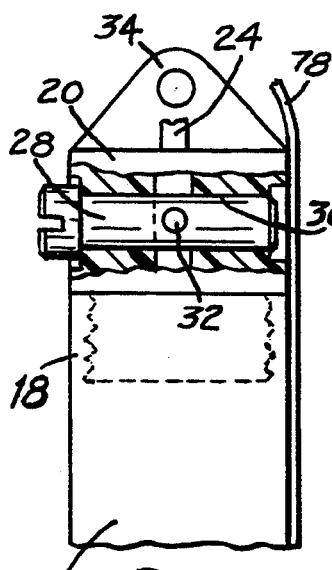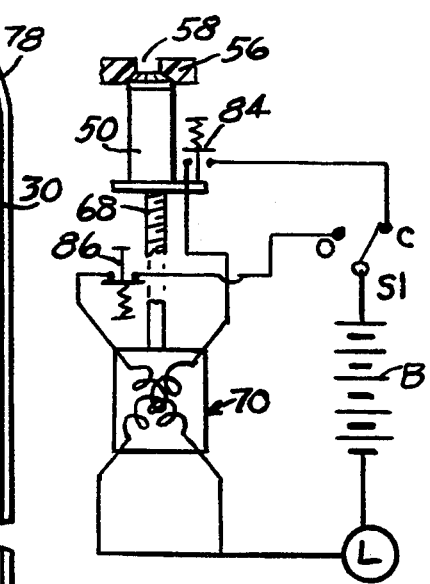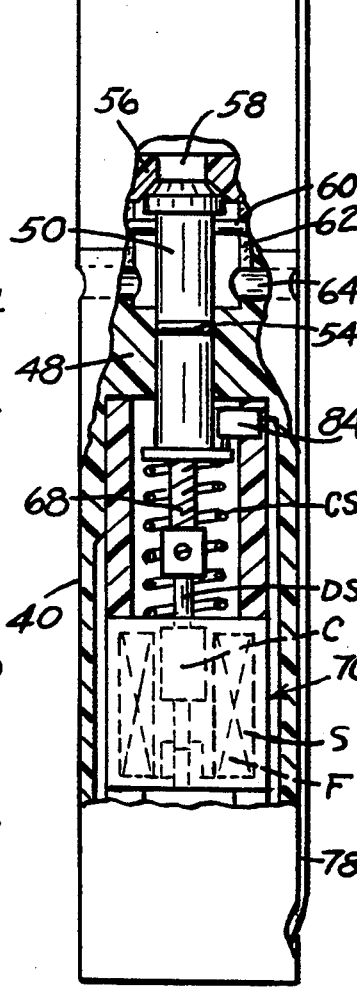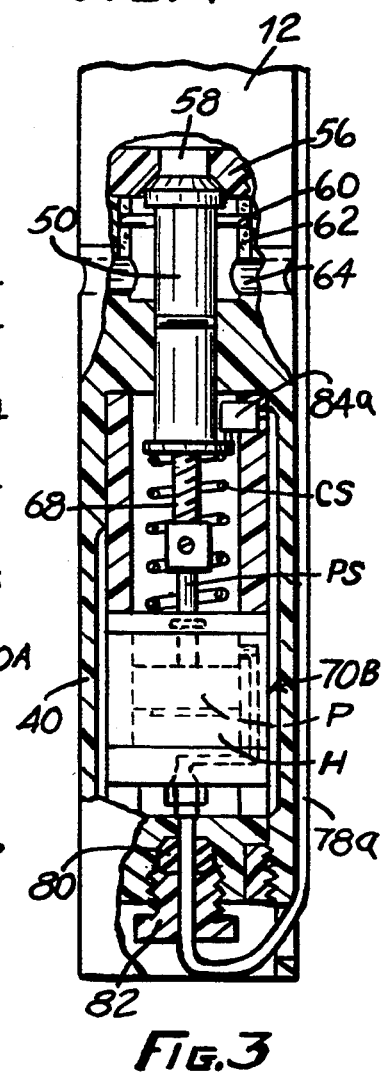
FIG.1  FIG.2  FIG.3  FIG.4

REMOTELY CONTROLLED SAMPLING DEVICE HAVING A VENT PASSAGE CONNECTING AN INTERNAL CHAMBER TO THE ENVIRONMENT THROUGH AN UPPER OUTLET

TECHNICAL DISCLOSURE

A simple fluid sampling device including a bailer provided with sealed in remotely controlled valve actuating means and by which true samples can be taken and sealed within the bailer at any depth, place, or level, within a body of fluid to be analyzed.

BACKGROUND OF THE INVENTION

1. Field of Invention

The invention relates to powered devices for taking and retrieving samples of fluid from any depth, level, or place within a body of fluid.

2. Description of the Prior Art

The prior art discloses many devices for taking samples of fluid at various depths and levels and usually provided with valve means that are manually or mechanically activated. A known electric sampling device is disclosed in U.S. Pat. No. 4,347,751 and comprises an exposed and unprotected system of pulleys or sprockets connected by belts or chains to a battery operated motor to open and close a pair of ball valves at opposite ends of a tubular body.

Another electrically controlled sampling device for taking samples at predetermined depths in a sea is disclosed in U.S. Pat. No. 3,625,066 and comprises a standard Nansen bottle with a pair of valves at its opposite ends connected to a slide rod and latches which are maintained in a latched position and movable under the influence of elastic bands. A surface powered low wattage resistor is connected to and retains the latches in a latched position to maintain valves open during its decent into the sea. At the desired depth the resistor is energized to release the latch and allow the elastic bands to act upon the rod and close the valves.

One disadvantage of the prior art devices is that the mechanism for operating the sampler are more complicated and mounted on the exterior of the main container and therefor exposed to and not protected from corrosive and toxic fluids. Another disadvantage of prior devices is that when the standard bailer is lowered into the fluid body every increment of its depth passes therethrough. In effect, the device is contaminated by the full volume of the body of fluid or liquid being sampled. If a small quantity (PPM or PPB) of a substance is later detected in the sample, it is not known whether it came from the lowest depth to which the device was lowered or from some intermediate depth.

The Applicants' device hereinafter disclosed is a true point-source device in that it can be lowered to any predetermined depth without entrance of fluid until it reaches the desired depth. At this depth an electric or fluid powered means is energized to open an inlet valve and allow the device to fill and air to vent. After a short period, the device is filled and the power means is reversed to close the inlet valve and seal a true representative uncontaminated sample of the fluid at the depth it was taken. Thus, the sample is sealed in the bailer and raised to the surface for analysis.

BRIEF DESCRIPTION OF THE DRAWINGS

FIG. 1 is a view partly in section of a sampling device with remotely actuated power means and valve means according to the invention;

FIG. 2 is another embodiment of a remotely actuated power means which may be substituted for the power means shown in FIG. 1;

FIG. 3 is still another embodiment of remotely actuated power means adaptable for use in the instant invention; and FIG. 4 is a diagrammatic view of a circuit for selectively energizing and deenergizing the power means and opening and closing the valve means shown in FIG. 1.

SUMMARY OF THE INVENTION

A remotely actuated sampling device which can take and retrieve samples from any depth within a body of fluid comprises valve means operated by electrical or fluid actuated power means sealed within a power chamber of a housing. The housing is sealingly connected to the lower end portion of an elongated tubular body or bailer for containing the sample. A valve chamber is situated in the housing adjacent to an outer sidewall with fluid passages therein and a valve seat with a valve passage therein extending to an internal chamber of the tubular body. An axially movable valve stem is sealingly mounted in and extends through a bore in the upper end wall of the power chamber and is connected to a feed screw and drive shaft of remotely actuated power means connected by power conductors of suitable type and length to extend above the surface of the body of fluid to a source of electricity or fluid under pressure necessary to operate the corresponding type of power means and move the valve stem into and out of engagement with the valve seat and thereby selectively open and close the valve passage to and from the internal chamber. An outlet end cap sealingly connected to the upper end portion of the tubular body or bailer is provided with a vent passage to which is sealingly connected a tubular vent conduit of sufficient length to extend above the surface of the body of fluid. The end cap is also provided with an eye or hook portion for attaching support means such as a cable, cord, or rod thereto for lowering and retrieving the sampling device into and from the body of fluid. A manually movable stop cock or valve may be provided in the outlet end cap to selectively close off or open an outlet or drain passage extending through the end cap from the internal chamber in the tubular bailer or body. It is, therefore, a primary object of the invention to provide a simple and dependable sampling device with remotely actuated power operated valve means for taking and retrieving uncontaminated samples from various depths and parts of a body of fluid.

DESCRIPTION OF THE PREFERRED EMBODIMENTS

In FIG. 1 there is shown a remotely actuated fluid sampling device 10 comprising a tubular body or bailer 12 the outer sidewall 14 of which surrounds an internal chamber 16 for receiving and containing a sample taken from a body of fluid. The tubular body 12 has a threaded upper outlet end portion 18 and a threaded lower inlet end portion 19.

An outlet end cap 20 is sealingly threaded to the upper outlet end portion 18 of the tubular bailer or body 12 and has a vent passage 22 therein extending from the internal chamber 16 and into which one end portion of a tubular conduit 24 is inserted into sealing engagement with the surfaces of the end cap about the vent passage 22. Conduit 24 extends upwardly from the end cap and is of sufficient length to allow an opposite open end thereof to extend to a position above the surface of the body of fluid from which a sample is taken. An outlet passage 26 is also provided in the outlet end cap 20 for draining the fluid sample from the internal chamber 16 and which is opened and closed off by a manually operable valve means such as a stop cock 28 movable in and sealingly engaging surfaces of a cross valve bore 30 in the end cap 20. A passage 32 in the valve 28 is selectively moved into and out of alignment with the outlet passage 26. At its upper end portion the end cap 20 is provided with connector means such as an eye or hook portion 34 for connecting a support line, cable or rod, of sufficient length thereto and by which the sampling device may be lowered into and retrieved from a body of fluid. Threadedly and sealingly connected to the internally threaded lower inlet end portion 19 of the tubular body 12 is a sealed housing 40 having an outer wall 42 extending around a sealed lower power chamber 44 and an upper valve chamber 46 separated by an upper end wall 48 of the power chamber 44. A valve stem 50 is slidably mounted in sealing engagement with the inner surface of a valve stem bore 52 extending through the upper end wall 48 between the valve and power chambers. An O-ring 54 in an annular groove around the valve stem engages the surface of the valve bore 52 and prevents leakage of fluid into the power chamber. At its upper end the valve stem 50 has a tapered end surface portion which engages and mates with the tapered surface of an annular valve seat 56 extending around a valve passage 58 and sealingly threaded into the upper end of valve chamber 46 and housing 40. In this instance the valve stem 50 is prevented from rotating by means of a key or pin 60 extending crosswise of the valve stem and into engagement with keyways 62 in opposite inner sides of the outer wall of valve chamber 46 and housing 40. At least one fluid passage 64 is provided in the outer side wall of housing about the valve chamber 46 for allowing fluid to pass to and from the valve chamber and into and out of the internal chamber 16 when the valve passage 58 is open and not obstructed by the valve stem 50. The lower end portion of the valve stem 50 has an elongated internally screw threaded bore 66 connected to and engaged by an externally threaded movable drive shaft or feed screw 68 coupled to a remotely actuated power means 70 sealed within the power chamber 44 of the housing 40.

The power means 70 may comprise a variety of remotely actuated rotary devices such as a reversible rotary electric, hydraulic or pneumatic motor all adapted to rotate the movable shaft 68, or axially movable devices such as an electromagnetic solenoid, a hydraulic or pneumatic piston or cylinder adapted to be connected to and move the drive shaft 68 axially. In all cases the movable drive shaft 68 whether rotated or moved axially by the devices mentioned hereinabove would be connected to and move the valve stem 50 into an out of engagement with the valve seat 56 in response to a signal from a remotely actuated means situated above the surface of a body of fluid.

As shown in FIG. 1 the power means 70 is preferably a small commercially available rotary electric motor adapted for connection to and rotate the movable screw threaded drive shaft 68 in opposite directions whereupon the nonrotatable valve stem 50 moves axially into and out of engagement with the valve seat 56.

The power means 70 is inserted into, held, and sealed within the power chamber 44 by retaining means including a retainer nut 72 sealingly threaded into the lower end of the housing 40 and forcing an end spacer or filler block 74 against an end of the outer casing of the power means 70 forced against an opposite end spacer 76.

A power conductor 78 of sufficient length to extend from a position above the surface of a body of fluid being sampled has one end connected to the power means and an adjacent portion passing through and sealingly connected to the end of the block or plug 74 by a grommet 80 sealingly compressed in an internally threaded bore and against the outer casing of the power conductor 78 and the bore by an annular retainer screw 82. In the case of electric power means 70 the power conductor 78 comprise suitably encased electrical conductors sealed within a single cable of desired length adapted to conduct power to the power means. In the case of pneumatic or hydraulic power means 70 the conductors are tubular and adapted to convey a fluid such as air, oil, or water under pressure to the power means.

Fixed to the interior of the upper annular insulating spacer 76 are a pair of limiting means 84 or 86 which are spaced apart, engaged by and actuated by axial movement of the lower flanged end portion of the valve stem 50. Actuating the limit means opens the power circuit to and stop movement of the power means and drive shaft at the end of each opposite axial movement of the valve stem indicating either the opening or closing of the valve passage 58. Actuation of limit means 84 opens circuits therein stopping the power means and indicates that the valve stem 50 has seated against the valve seat 56 and closed the passage 58. Limit means 86 is actuated to open the circuit and stop the power means and indicate opening of the valve passage when the valve stem has moved a predetermined distance from the valve seat 56. As shown in FIG. 4, each of the limit means 84 and 86 has a pair of normally closed contacts which are wired in series with the reversible windings of the electric motor or solenoid power means and an indicator light L which goes out when the limit switch is opened to stop the power means 70.

The sampling device 10 is prepared for use by first closing the stop cock valve 28 and outlet passage and energizing the power means 70 to move the valve stem 50 axially and close the valve passage 58. A support line may be required and connected to the eye portion 34 for lowering and retrieving the device. However, in some instances, it maybe supported by utilizing the vent conduit 24 and the power conductor 78 attached to one another.

With the valve passage 58 closed the sampling device is then lowered into the body of fluid to the depth being investigated. At the desired depth the power means 70 is actuated by moving switch S1 connected to power supply means such as a battery B located above the surface of the fluid to position O to cause the power means 70 to retract the valve stem 50 and open the valve passage 58. Fluid now passes through the fluid passages 64 into the valve chamber 46 and through the valve passage 58 to the internal chamber 16 whereupon the atmosphere or air exhausts from the internal chamber through the tubular vent 24. During retraction of the valve stem 50 away from the valve seat 56 limiting means 84 closes and valve indicator means such as a light L, shown in FIG. 4, is actuated until the valve stem 50 is fully retracted whereupon it contacts the normally closed limiting device 86 which opens the power supply circuit to and stops both the valve indicator and power means 70. Following a short predetermined period of time the internal chamber 16 in tubular body 12 is deemed to be full, the reversible power means 70 is actuated by moving switch S1 to position C to supply power and move the power means and valve stem 50 in the opposite direction and close the passage 58. Movement of the valve stem 50 against the valve seat 56 opens the normally closed limiting device 84 to stop both the valve indicator L and power means 70. The sampling device is then retrieved and pulled upwardly out of the body of fluid whereupon the fluid contents may be emptied by either operating the power means and reopening the bottom valve passage 58 or by opening the outlet stop cock 28 and passage 26 in the outlet end cap.

In FIG. 2 there is shown another embodiment of the invention wherein the valve stem 50 is connected to and moved by axially movable power means 70A comprising a one way pull type electro magnetically actuated solenoid S commercially available from various sources. An axially movable drive shaft DS extends from the armature or core C attracted by the field coil F of the solenoid S and is coupled to the screw shaft 68 adjustably fixed to the valve stem 50.

A spring CS situated between the body of the solenoid S and the end of the valve stem 50 normally biases the valve stem 50 against the valve seat 56 and closes the valve passage 58. When the device 10 equipped with the solenoid power means 70A is lowered to the desired depth in a body of fluid a simple circuit including a main switch connected to a source of electricity such as a battery is closed whereupon the field of the solenoid CS is energized which pulls the core C, a fixed axial amount. Downward axial movement of the core C and attached drive shaft DS coupled to screw shaft 68 retracts the valve stem 50 and opens the valve passage 58. Optionally the normally closed switch 84 maybe connected in parallel with the main switch to the source of electricity and in series with indicator means such as a light. The switch 84 will close when the valve stem 50 moves away whereupon the indicator means will indicate opening of the valve passage 58. After a period of time deemed to be sufficient to fill the internal chamber the main switch is opened to deenergize the solenoid S whereupon the previously compressed spring CS forces the valve stem 50 axially to close the valve passage 58. Axial movement of the valve stem 50 upwardly activates the limit switch means 84 which opens the circuit to the valve indicator means and tells the operator that the valve passage 58 is closed and the device with a fluid sample therein may be retrieved to the surface.

Optionally the power means 70A may also comprise a commercially available two-way solenoid wherein the core and drive shaft thereof are moveable in opposite directions. Hence a two way solenoid would likewise move the valve stem 50 in opposite directions to open and close the valve passage 58.

Similarly shown in FIG. 3 is another embodiment of the sampling device in which the remotely activated power means 70B sealed within the housing 40 comprises an axially movable fluid operated piston P and cylinder or housing H. A sealed piston rod or drive shaft PS extends from the piston P and is fixedly attached or coupled to the screw threaded drive shaft 68 adjustably fixed to the valve stem 50. The compressible coil spring CS extends between the cylinder or housing H and biases the valve stem 50 into engagement with the valve seat 56 and closes the valve passage 58. A tubular fluid conduit 78a is provided instead of an electrical conductor for conducting fluid from an above provided source of fluid under pressure into the cylinder housing H for moving the piston P and valve stem 50 away from the valve seat 56. A suitable source of fluid under pressure maybe a small tank of compressed air or hydraulic oil under pressure. All that is needed to operate the power means 70B and valve stem 50 is to connect the tubular fluid conductor to actuating means such as a valve connected to the tank of fluid under pressure situated above the surface of the body of fluid. Optionally, the fluid conductor 78a maybe connected to a portable manually or electrically operated fluid pump. When the device is lowered to the desired depth in a body of fluid, opening either the valve of the tank or starting the fluid pump allows fluid under pressure into the conduit 78a and the cylinder housing H and forces the piston P downwardly a predetermined axial distance to the end of the cylinder. Movement of the piston P, drive shaft PS and attached valve stem 50 compresses the spring CS and opens passage 58. After filling of the internal chamber 16 the fluid conductor 78a is disconnected by any suitable means from the source of fluid under pressure whereby the compressed spring CS will move the piston upwardly and exhaust fluid through the conduit 78a and move the valve stem 50 into engagement with the valve seat and close the valve passage 58. If desired, a fluid operated switch 84a or valve may be provided in place of the electrical switch 84 to operate valve indicator means as taught above with reference to the solenoid type power means 70A of FIG. 2.

The power means 70B may also be substituted for by a double acting or two way fluid operated piston and cylinder or by a reversible rotary fluid motor connected by fluid conduits to operate in a manner similar to the rotary electric power means 70 shown in FIG. 1.

The various components of the sampling device 10 other than the power means sealed within the power chamber 44 of the housing 40 are preferably made of chemically inert materials which are not affected by the types of fluid from which samples are to be taken. For example, the tubular body 12, end cap 20, vent tube 24, valve 28, housing 40, and associated valve stem 40, valve seat 56, filler block 74, retainer 72 and compression screw or bolt 82, are all preferably made of a fluoropolymer material selected from polytetrafluoroethylene and tetrafluoroethylene or other materials coated therewith. However, they may in some instances be made of other materials selected from a group consisting of polypropylene, ceramic, glass, stainless steel, aluminum, and combinations thereof.

We claim:

1. A remotely actuated sampling device for retrieving a sample from a predetermined depth in a body of fluid comprising:

an elongated tubular body having:
an outer sidewall extending around an internal chamber and between a lower inlet end portion and an upper outlet end portion of the tubular body; an outlet end cap sealingly connected to and extending from the upper outlet end portion of the tubular body and having a vent passage extending therethrough and connected to the internal chamber;

a tubular conduit having a lower end portion sealingly connected to the vent passage and the outlet end cap and of sufficient length to extend upwardly and position an upper end thereof above the body of fluid;

a sealed housing sealingly connected to and extending from the lower end portion of the tubular body and having an outer wall extending around a lower sealed power chamber and an upper valve chamber separated by an upper end wall of the sealed power chamber;

remotely actuated power means sealed within the power chamber including a movable drive shaft;

power conductors sealingly connected to the housing and of sufficient length to extend from the power means to a source of energy situated above the body of fluid;

a valve seat including a valve passage therein sealingly connected to an upper end portion of the housing above the upper valve chamber and a fluid passage in the outer sidewall of the housing around the upper valve chamber;

an axially movable valve stem connected to and movable by the drive shaft into and out of engagement with the valve seat, and said valve stem extending through and sealed relative to the internal surfaces of a bore in the upper end wall of the housing.

2. A sampling device according to claim 1 further comprising:

an outlet passage extending through the end cap from the internal chamber, and manually operable valve means for selectively opening and closing off the outlet passage.

3. A sampling device according to claim 2 further comprising:

connector means on the end cap for attaching support means thereto for lowering and retrieving the sampling device into and from the body of fluid.

4. A sampling device according to claim 1 further comprising:

limiting means for stopping the power means at the end of each axial movement of the valve stem supported within the housing adjacent to and actuated by a lower end portion of the valve stem.

5. A sampling device according to claim 1 wherein the power means comprises:

a reversible electric motor connected to and adapted to rotate the drive shaft screw threaded to the axially movable valve stem.

6. A sampling device according to claim 1 wherein the power means comprises:

an electric solenoid connected to and adapted to axially move the drive shaft and the axially movable valve stem.

7. A sampling device according to claim 1 wherein the power means comprises:

fluid operated means connected to and adapted to move the drive shaft and the power conductors are tubular fluid conduits.

8. A sampling device according to claim 7 wherein the fluid operated means comprises:

a reversibly fluid motor adapted to rotate the drive shaft screw threaded to the axially movable valve stem.

9. A sampling device according to claim 7 wherein the fluid operated means comprise a fluid cylinder having a piston and a piston rod connected to the drive shaft and the axially movable valve stem.

* * * * *